United States Patent

Epstein et al.

Patent Number: 5,932,585
Date of Patent: Aug. 3, 1999

[54] METHOD OF TREATING OR INHIBITING NEUTROPENIA

[75] Inventors: Joseph W. Epstein, Monroe; Jeremy I. Levin, Nanuet, both of N.Y.; James J. Gibbons, Westwood, N.J.; Judy Lucas, Nanuet, N.Y.

[73] Assignee: American Cyanamid Company, Madison, N.J.

[21] Appl. No.: 08/991,424

[22] Filed: Dec. 16, 1997

Related U.S. Application Data

[60] Provisional application No. 60/032,448, Dec. 19, 1996.

[51] Int. Cl.$^6$ .......................... A61K 31/505; A61K 31/55
[52] U.S. Cl. ............................................. 514/267; 514/212
[58] Field of Search ...................... 514/212, 267

[56] References Cited

U.S. PATENT DOCUMENTS 4,713,383  12/1987  Francis et al. ........................... 514/267
4,916,137  4/1990   Epstein et al. ........................... 514/267

FOREIGN PATENT DOCUMENTS 0674585  11/1963  Canada.

*Primary Examiner*—Kimberly Jordan
*Attorney, Agent, or Firm*—Arnold S. Milowsky

[57] ABSTRACT

The invention is a method of treating or inhibiting neutropenia, or accelerating neutrophil recovery in a mammal in need thereof, which comprises administering to said mammal an effective amount of a compound having the formula:

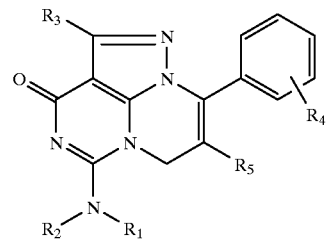

wherein $R_1$ and $R_2$ are each, independently selected from the group consisting of hydrogen, alkyl of 1–6 carbon atoms, optionally substituted benzoyl,

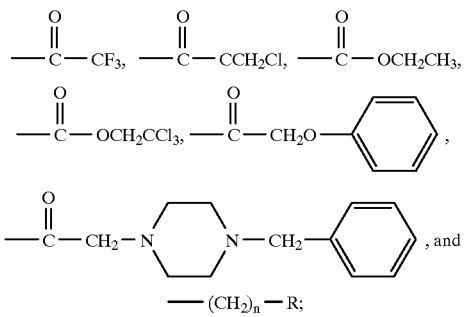

$-(CH_2)_n-R$;

or $R_1$ and $R_2$ are methylene groups which are taken together to form a 4–7 membered saturated heterocyclic ring;

R is hydroxy, 4-morpholinyl, 1H-imidazol-1-yl, —CH (alkoxy of 1–6 carbon atoms)$_2$, α-hydroxybenzyl, or optionally substituted phenyl;

$R_3$ is hydrogen or alkyl; $R_4$ is hydrogen, halogen, alkyl, alkoxy, or trifluoromethyl; $R_5$ is hydrogen or alkyl; and n=1–3, or a pharmaceutically acceptable salt thereof.

3 Claims, No Drawings

METHOD OF TREATING OR INHIBITING NEUTROPENIA

This application claims the benefit of U.S. Provisional Application No. 60/032,448, filed Dec. 19, 1996.

BRIEF SUMMARY OF THE INVENTION

This invention provides a method of treating or inhibiting neutropenia in a mammal in need thereof, which comprises administering to said mammal an effective amount of a compound having the formula:

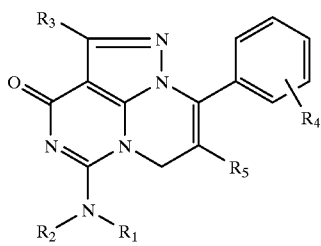

wherein $R_1$ and $R_2$ are each, independently selected from the group consisting of hydrogen, alkyl of 1–6 carbon atoms, benzoyl,

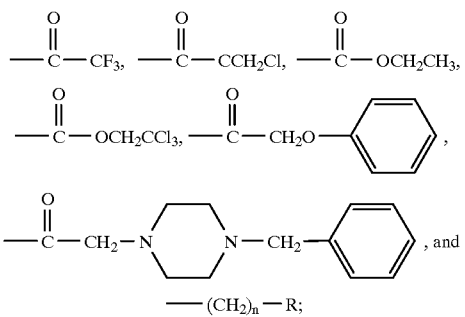

or $R_1$ and $R_2$ are methylene groups which are taken together to form a 4–7 membered saturated heterocyclic ring; wherein when $R_1$ or $R_2$ is benzoyl, the phenyl ring of the benzoyl moiety may be optionally mono- or di-substituted with a substituent selected from the group consisting of alkyl of 1–6 carbon atoms, alkoxy of 1–6 carbon atoms, acyloxy of 2–7 carbon atoms, halogen, nitro, and trifluoromethyl;

R is hydroxy, 4-morpholinyl, 1H-imidazol-1-yl, —CH (alkoxy of 1—6 carbon atoms)$_2$, α-hydroxybenzyl, or phenyl; wherein the phenyl ring may be optionally substituted with a substituent selected from the group consisting of halogen and alkyl of 1–6 carbon atoms;

$R_3$ is hydrogen or alkyl of 1–6 carbon atoms;

$R_4$ is hydrogen, halogen, alkyl of 1–6 carbon atoms, alkoxy of 1–6 carbon atoms, or trifluoromethyl;

$R_5$ is hydrogen or alkyl of 1–6 carbon atoms; and n=1–3, or a pharmaceutically acceptable salt thereof.

As used in describing this invention, the term alkyl includes both straight chain as well as branched moieties. The term halogen includes fluorine, chlorine, bromine, and iodine.

The pharmaceutically acceptable salts are those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methanesulfonic, toluenesulfonic and similarly known acceptable acids.

As used in accordance with this invention, treating covers treatment of an existing condition, ameliorating the condition, or providing palliation of the condition and inhibiting includes inhibiting or preventing the progress or development of the condition.

DETAILED DESCRIPTION OF THE INVENTION

The preparation of the compounds of this invention is described in U.S. Pat. No. 4,916,137, which is hereby incorporated herein by reference.

The ability of the compounds of this invention to treat or inhibit neutropenia was evaluated in the 5-fluorouracil (5-FU) induced neutropenia standard pharmacological test procedure which measures a compound's ability to enhance neutrophil recovery post chemotherapy. Based on the results obtained in this test procedure, the compounds of this invention demonstrated a substantial acceleration of neutrophil recovery following administration of 5-FU. The test procedure used and results obtained with a representative compound of this invention are provided below.

Briefly, C3HHeb/Fej male mice, 8–10 weeks of age, were used to evaluate the ability of a compound to accelerate neutrophil recovery post chemotherapy. The mice were routinely housed for ten days prior to testing in order to stabilize their immune responses. The mice were housed 5-per-cage and received food and water ad libitum throughout the experiment. Fluorouracil injection, 500 mg/10 ml, was diluted in phosphate-buffered saline for intraperitoneal injection at 150 mg/kg, 0.5 cc. Twenty-four hours following 5-FU, the mice were treated with either vehicle or a representative compound of this invention, which was mixed in 0.2% Klucel and sonicated, resulting in a milky white suspension, and 0.2 cc was administered for subcutaneous or oral dosing and 0.5 cc when the compound is dosed intraperitoneally. Compound was either given as a single injection 24 hours following 5-FU, or as multiple daily doses for 10 days beginning 24 hours following 5-FU. A neutrophil recovery curve following 5-FU administration was generated by measuring circulating neutrophils. Mice were retroorbitally bled and a 20 µl sample was taken for measurement of total white blood cells using a Coulter Counter. In addition, a blood smear was also prepared. The slides were stained using Diff-Quick and the percent neutrophils was determined by scoring 100, stained, white-blood-cells. The total number of neutrophils per cubic mm was calculated and plotted against time (days post 5-FU).

A dose-related acceleration of neutrophil recovery following 5-FU in mice results from subcutaneous treatment with compound of Example 14 as shown in Table I. The compound of Example 14, when dosed either subcutaneously or intraperitoneally, is effective in accelerating neutrophil recovery after 5-fluorouracil treatment in mice as shown in Table II.

TABLE I

A dose-related acceleration of neutrophil recovery following 5-fluorouracil (5-FU) in mice results from subcutaneous treatment with compound of Example 14

| Days Post 5-FU TREATMENT | 7 | 8 Neutrophils/mm$^3$ | 9 |
|---|---|---|---|
| 0.2% Klucel | 32 ± 14 | 363 ± 86 | 881 ± 77 |
| 200 mg/kg | 213 ± 49 | 738 ± 91 | 1951 ± 388 |
| 100 mg/kg | 160 ± 39 | 961 ± 148 | 1833 ± 253 |
| 50 mg/kg | 166 ± 38 | 753 ± 134 | 966 ± 143 |
| 25 mg/kg | 76 ± 19 | 540 ± 104 | 1193 ± 232 |

TABLE II

Compound of Example 14, when dosed either subcutaneously or intraperitoneally, is effective in accelerating neutrophil recovery after 5-fluorouracil treatment in mice

| Days Post 5-FU TREATMENT | 7 | 8 Neutrophils/mm$^3$ | 9 |
|---|---|---|---|
| none | 130 ± 52 | 923 ± 419 | 1884 ± 812 |
| 50 mg/kg, sc | 798 ± 160 | 2979 ± 400 | 4178 ± 625 |
| 50 mg/kg, ip | 733 ± 133 | 2600 ± 395 | 3423 ± 343 |

Based on the results of these standard pharmacological test procedures, the compounds of this invention are useful as agents for the treatment or inhibition of neutropenia, particularly following chemotherapy, when administered in amounts ranging from about 5 mg to about 200 mg/kg of body weight per day. A preferred dosage regimen for optimum results would be from about 10 mg to about 50 mg/kg of body weight per day and such dosage units are employed that a total of from about 700 mg to about 3.5 g of the active compound for a subject of about 70 kg of body weight are administered in a 24 hour period.

The dosage regimen for treating neutropenia in mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The following are representative examples of compounds of this invention which are useful in treating or inhibiting neutropenia. The preparation of these compounds are described in U.S. Pat. No. 4,916,137, which is hereby incorporated by reference.

EXAMPLE 1

7-[3-(Trifluoromethyl)phenyl]pyrazolo[1,5-a]-pyrimidine-3-carboxamide

EXAMPLE 2

7-Phenylpyrazolo[1,5-a]pyrimidine-3-carboxamide

EXAMPLE 3

4,5-Dihydro-7-phenylpyrazolo[1,5-a]pyrimidine-3-carboxamide

EXAMPLE 4

4,5-Dihydro-7-[3-(trifluoromethyl)phenyl]pyrazolo[1,5-a]pyrimidine-3-carboxamide

EXAMPLE 5

7-(3-Fluorophenyl)pyrazolo[1,5-a]pyrimidine-3-carboxamide

EXAMPLE 6

7-(3-Fluorophenyl)-4,5-dihydropyrazolo[1,5-a]pyrimidine-3-carboxamide

EXAMPLE 7

4,5-Dihydro-8-phenyl-5-thioxo-3H,6H-1,4,5a,8a-tetraazaacenaphthylen-3-one

EXAMPLE 8

4,5-Dihydro-5-thioxo-8-[3-(trifluoromethyl)phenyl]-3H,6H-1,4,5a,8a-tetraazaacenaphthylen-3-one.

EXAMPLE 9

5-(Methylthio)-8-[3-(trifluoromethyl)phenyl]-3H,6H-1,4,5a,8a-tetraazaacenaphthylen-3-one

EXAMPLE 10

8-(3-Fluorophenyl)-4,5-dihydro-5-thioxo-3H,6H-1,4,5a,8a-tetraazaacenaphthylen-3-one

EXAMPLE 11

N-[3-Oxo-8-[3-(trifluoromethyl)phenyl]-3H,6H-1,4,5a,8a-tetraazaacenaphthylen-5-yl]benzamide

EXAMPLE 12

[[3-(Aminocarbonyl)-7-[3-(trifluoromethyl)phenyl]pyrazolo[1,5-a]pyrimidin-4(5H)-yl]-thioxomethyl]carbamic acid, ethyl ester

EXAMPLE 13

[3-Oxo-8[3-(trifluoromethyl)phenyl]-3H,6H-1,4,5a,8a-tetraazaacenaphthylen-5-yl]carbamic acid, ethyl ester

EXAMPLE 14

5-(2-Methylpropyl)-8-[3-(trifluoromethyl)phenyl]-3H,6H-1,4,5a,8a-tetraazaacenaphthylen-3-one

EXAMPLE 15

5-(1-Pyrrolidinyl)-8-[3-(trifluoromethyl)phenyl]-3H,6H-1,4,5a,8a-tetraazaacenaphthylen-3-one

EXAMPLE 16

5-[(1-Methylethyl)amino]-8-[3-(trifluoromethyl)phenyl]-3H,6H-1,4,5a,8a-tetraazaacenaphthylen-3-one

EXAMPLE 17

5-[(2,2-Dimethoxyethyl)amino]-8-[3-(trifluoromethyl)phenyl]-3H,6H-1,4,5a,8a-tetraazaacenaphthlen-3-one

EXAMPLE 18

5-[(1-Methylpropyl)amino]-8-[3-(trifluoromethyl)phenyl]-3H,6H-1,4,5a,8a-tetraazaacenaphthylen-3-one

EXAMPLE 19

5-(1-Piperidinyl)-8-[3-(trifluoromethyl)phenyl]-3H,6H-1,4,5a,8a,tetraazaacenaphthylen-3-one

EXAMPLE 20

5-[[2-(4-Morpholinyl)ethyl]amino]-8-[3-(trifluoromethyl)phenyl]-3H,6H-1,4,5a,8a-tetraazaacenaphthylen-3-one

EXAMPLE 21

5-[(2-Hydroxy-2-phenylethyl)amino]-8-[3-(trifluoromethyl)phenyl]-3H,6H-1,4,5a,8a-tetraazaacenaphthylen-3-one

EXAMPLE 22

5-(Butylamino)-8-[3-(trifluoromethyl)phenyl]-3H,6H-1,4,5a,8a-tetraazaacenaphthylen-3-one

EXAMPLE 23

5-[(2-Hydroxyethyl)amino]8-[3-(trifluoromethyl)phenyl]-3H,6H-1,4,5a,8a-tetraazaacenaphthtylen-3-one

EXAMPLE 24

5-(Methylamino)-8-[3-(trifluoromethyl)phenyl]-3H,6H-1,4,5a,8a-tetraazaacenaphthylen-3-one

EXAMPLE 25

5-[[(2-Methylphenyl)methyl]amino]-8-[3-(trifluoromethyl) phenyl]-3H,6H-1,4,5a-8a-tetraazaacenaphylen-3-one

EXAMPLE 26

5-(4-Morpholinyl)-8-[3-(trifluoromethyl)phenyl]-3H,6H-1,4,5a,8a-tetraazaacenaphthylen-3-one

EXAMPLE 27

5-Ethylamino-8-[3-(trifluoromethyl)phenyl]-3H,6H-1,4,5a,8a-tetraazaacenaphthylen-3-one

EXAMPLE 28

5-[(Phenylmethyl)amino]-8-[3-(trifluoromethyl)phenyl]-3H,6H-1,4,5a,8a-tetraazaacenaphthylen-3-one

EXAMPLE 29

5-Amino-8-[3-(trifluoromethyl)phenyl]-3H,6H-1,4,5a,8a-tetraazaacenaphthylen-3-one

EXAMPLE 30

2,2,2-Trifluoro-N-[3-oxo-8-[3-(trifluoromethyl)phenyl]-3H,6H-1,4,5a,8a-tetraazaacenaphthylen-5-yl]acetamide

EXAMPLE 31

2-Chloro-N-[3-oxo-8-[3-(trifluoromethyl)phenyl]-3H,6H-1,4,5a,8a-tetraazaacenaphthylen-5-yl]acetamide

EXAMPLE 32

[3-Oxo-8-[3-(trifluoromethyl)phenyl]-3H,6H-1,4,5a,8a-tetraazaacenaphthylen-5-yl) carbamic acid, 2,2,2-trichloroethyl ester

EXAMPLE 33

4-Methoxy-N-[3-oxo-8-[3-(trifluoromethyl)phenyl]-3H,6H-1,4,5a,8a-tetraazaacenaphthylen-5-yl]benzamide

EXAMPLE 34

N-[3-Oxo-8-[3-(trifluoromethyl)phenyl]-3H,6H-1,4,5a,8a-tetraazaacenaphthylen-5-yl]-3-(trifluoromethyl)benzamide

EXAMPLE 35

4-Methyl-N-[3-oxo-8-[3-(trifluoromethyl)phenyl]-3H,6H-1,4,5a,8a-tetraazaacenaphthylen-5-yl]benzamide

EXAMPLE 36

2-(Acetyloxy)-N-[3-oxo-8-[3-(trifluoromethyl)phenyl]-3H,6H-1,4,5a,8a-tetraazaacena-phthylen-5-yl]benzamide

EXAMPLE 37

N-[3-Oxo-8-[3-(trifluoromethyl)phenyl]-3H,6H-1,4,5a,8a-tetraazaacenaphthylen-5-yl]-phenoxyacetamide

EXAMPLE 38

5-Methoxy-N-[3-oxo-8-[3-(trifluoromethyl)phenyl]-3H,6H-1,4,5a,8a-tetraazaacenaphthylen-5-yl]benzamide

EXAMPLE 39

3-Nitro-N-[3-oxo-8-[3-(trifluoromethyl)phenyl]-3H,6H-1,4,5a,8a-tetraazaacenaphthylen-5-yl]benzamide

EXAMPLE 40

4-Bromo-N-[3-oxo-8-[3-(trifluoromethyl)phenyl]-3H,6H-1,4,5a,8a-tetraazaacenaphthylen-5-yl]benzamide

EXAMPLE 41

3,4-Dichloro-N-[3-oxo-8-[3-(trifluoromethyl)phenyl]-3H,6H-1,4,5a,8a-tetraazaacenaphthylen-5-yl]benzamide

EXAMPLE 42

4-Fluoro-N-[3-oxo-8-[3-(trifluoromethyl)phenyl]-3H,6H-1,4,5a,8a-tetraazaacenaphthylen-5-yl]benzamide

EXAMPLE 43

5-[[(4-Chlorophenyl)methyl]amino]-8-[3-(trifluoromethyl)phenyl]-3H,6H-1,4,5a,8a-tetraazaacenaphthylen-3-one

EXAMPLE 44

5-[(2-Methylpropyl)amino]-8-phenyl-3H,6H-1,4,5a,8a-tetraazaacenaphthylen-3-one

EXAMPLE 45

5-[(2,2-Dimethoxyethyl)amino]-8-phenyl-3H,6H-1,4,5a,8a-tetraazaacenaphthylen-3-one

EXAMPLE 46

5-(Butylamino)-8-phenyl-3H,6H-1,4,5a,8a-tetraazaacenaphthylen-3-one

EXAMPLE 47

5-Amino-8-phenyl-3H,6H-1,4,5a,8a-tetraazaacenaphthylen-3-one

EXAMPLE 48

5-(Ethylamino)-8-phenyl-3H,6H-1,4,5a,8a-tetraazaacenaphthylen-3-one

EXAMPLE 49

5-[(Methylethyl)amino]-8-phenyl-3H,6H-1,4,5a,8a-tetraazaacenaphthylen-3-one

EXAMPLE 50

5-[(2-Hydroxyethyl)amino]-8-phenyl-3H,6H-1,4,5a,8a-tetraazaacenaphthylen-3-one

EXAMPLE 51

5-(Methylamino)-8-phenyl-3H,6H-1,4,5a,8a-tetraazaacenaphthylen-3-one

EXAMPLE 52

8-(3-Fluorophenyl)-5-[(2-methylpropyl)amino]-3H,
6H-1,4,5a,8a-tetraazaacenaphthylen-3-one

EXAMPLE 53

5-(Butylamino)-8-(3-fluorophenyl)-3H,6H-1,4,5a,
8a-tetraazaacenaphthylen-3-one

EXAMPLE 54

8-(3-Fluorophenyl)-5-[(1-amine methylpropyl)
amino]-3H,6H-1,4,5a,8a-tetraazaacenaphthylen-3-
one

EXAMPLE 55

5-(Ethylamino)-8-(3-fluorophenyl)-3H,6H-1,4,5a,8a-
tetraazaacenaphthylen-3-one

EXAMPLE 56

5-[(2,2-Dimethoxyethyl)amino]-8-(3-fluorophenyl)-
3H,6H-1 ,4,5a,8a-tetraazaacenaphthylen-3-one

EXAMPLE 57

8-(3-Fluorophenyl)-5-[(1 -methylethyl)amino]-3H,
6H-1,4,5a,8a-tetraazaacenaphthylen-3-one

EXAMPLE 58

8-(3-Fluorophenyl)-5-[[3-( 1 H-imidazol-1 -yl)
propyl]amino]-3H,6H-1,4,5a,8a-
tetraazaacenaphthylen-3-one

EXAMPLE 59

5-[[3-(1H-Imidazol-1-yl)propyl]amino]-8-phenyl-
3H,6H-1,4,5a,8a-tetraazaacenphthylen-3-one

EXAMPLE 60

5-Amino-8-(3-fluorophenyl)-3H,6H-1,4,5a,8a-
tetraazaacenaphthylen-3-one

EXAMPLE 61

N-[3-Oxo-8-[3-(trifluoromethyl)phenyl]-3H,6H-1,4,
5a,8a-tetraazaacenaphthylen-5-yl]-4-(phenylmethyl)-
1-piperazineacetamide

EXAMPLE 62

7-Methyl-5-[(1-methylethyl)amino]-8-[3-
(trifluoromethyl)phenyl]-3H,6H-1,4,5a,8a-
tetraazaacenaphthylen-3-one

EXAMPLE 63

8-(4-Chlorophenyl)-7-methyl-5-[(2-methylpropyl)
amino)-3H,6H-1,4,5a,8a-tetraazaacenaphthylen-3-
one

EXAMPLE 64

5-(Butylamino)-2,7-dimethyl-8-phenyl-3H,6H-1,4,
5a,8a-tetraazaacenaphthylen-3-one

EXAMPLE 65

7-(3-methylphenyl)pyrazolo[1,5-a]pyrimidine-3-
carboxamide

EXAMPLE 66

4,5-Dihydro-7-(3-methylphenyl)pyrazolo[1,5-a]
pyrimidine-3-carboxamide

EXAMPLE 67

4,5-Dihydro-5-thioxo-8-)3-methylphenyl)-3H,6H-1,
4,5a,8a-tetraazaacenaphthylen-3-one

EXAMPLE 68

8-(3-Methylphenyl)-5-[(2-methylpropyl)amino]-3H,
6H-1,4,5a,8a-tetraazaacenaphthylen-3-one

EXAMPLE 69

7-(3-Methoxyphenyl)pyrazolo[1,5-a]pyrimidine-3-
carboxamide

EXAMPLE 70

4,5-Dihydro-7-(3-methoxyphenyl)pyrazolo[1,5-a]
pyrimidine

EXAMPLE 71

4,5-Dihydro-8-(3-methoxyphenyl)-5-thioxo-3H,6H-
1,4,5a,8a-tetraazaacenaphthylen-3-one

EXAMPLE 72

8-(3-Methoxyphenyl)-5-[2-methylpropyl)amino]-3h,
6H-1,4,5a,8a-tetraazaacenaphthylen-3-one

We claim:

1. A method of treating or inhibiting neutropenia in a mammal in need thereof, which comprises administering to said mammal an effective amount of a compound having the formula:

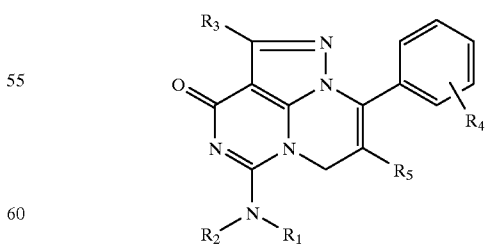

wherein $R_1$ and $R_2$ are each, independently selected from the group consisting of hydrogen, alkyl of 1–6 carbon atoms, benzoyl,

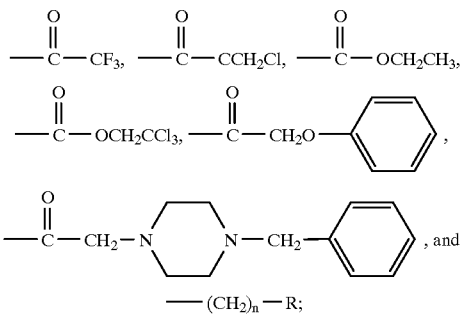

or $R_1$ and $R_2$ are methylene units which are taken together to form a 4–7 membered saturated heterocyclic ring, wherein $R_1$ and $R_2$ together contain from 3–6 methylene units;

wherein when $R_1$ or $R_2$ is benzoyl, the phenyl ring of the benzoyl moiety may be optionally mono- or di-substituted with a substituent selected from the group consisting of alkyl of 1–6 carbon atoms, alkoxy of 1–6 carbon atoms, acyloxy of 2–7 carbon atoms, halogen, nitro, and trifluoromethyl;

R is hydroxy, 4-morpholinyl, 1H-imidazol-1-yl, —CH(alkoxy of 1–6 carbon atoms)$_2$, α-hydroxybenzyl, or phenyl; wherein the phenyl ring may be optionally substituted with a substituent selected from the group consisting of halogen and alkyl of 1–6 carbon atoms;

$R_3$ is hydrogen or alkyl of 1–6 carbon atoms;

$R_4$ is hydrogen, halogen, alkyl of 1–6 carbon atoms, alkoxy of 1–6 carbon atoms, or trifluoromethyl;

$R_5$ is hydrogen or alkyl of 1–6 carbon atoms; and n =1–3, or a pharmaceutically acceptable salt thereof.

2. The method of claim 1 wherein said compound is 5-(2-methylpropyl)-8-[3-(trifluoromethyl)phenyl]-3H,6H-1,4-5a,8a-tetraazaacenaphthylen-3-one or 5-amino-8-[3-(trifluoromethyl)phenyl]-3H,6H-1,4,5a,8a-tetraazaacenaphthylen-3-one.

3. A method of accelerating neutrophil recovery in a mammal in need thereof, which comprises administering to said mammal an effective amount of a compound having the formula:

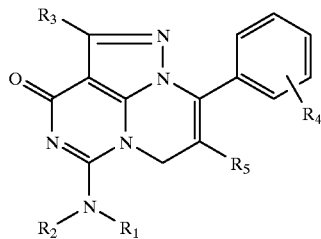

wherein
$R_1$ and $R_2$ are each, independently selected from the group consisting of hydrogen, alkyl of 1–6 carbon atoms, benzoyl,

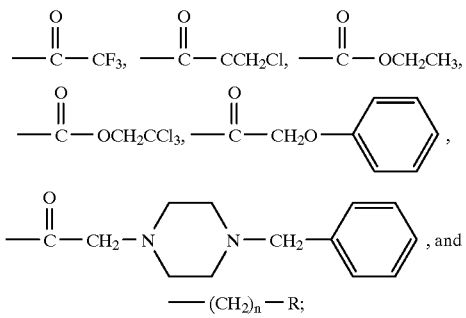

or $R_1$ and $R_2$ are methylene units which are taken together to form a 4–7 membered saturated heterocyclic ring, wherein $R_1$ and $R_2$ together contain from 3–6 methylene units;

wherein when $R_1$ or $R_2$ is benzoyl, the phenyl ring of the benzoyl moiety may be optionally mono- or di-substituted with a substituent selected from the group consisting of alkyl of 1–6 carbon atoms, alkoxy of 1–6 carbon atoms, acyloxy of 2–7 carbon atoms, halogen, nitro, and trifluoromethyl;

R is hydroxy, 4-morpholinyl, 1H-imidazol-1-yl, —CH(alkoxy of 1–6 carbon atoms)$_2$, α-hydroxybenzyl, or phenyl; wherein the phenyl ring may be optionally substituted with a substituent selected from the group consisting of halogen and alkyl of 1–6 carbon atoms;

$R_3$ is hydrogen or alkyl of 1–6 carbon atoms;

$R_4$ is hydrogen, halogen, alkyl of 1–6 carbon atoms, alkoxy of 1–6 carbon atoms, or trifluoromethyl;

$R_5$ is hydrogen or alkyl of 1–6 carbon atoms; and n =1–3, or a pharmaceutically acceptable salt thereof.

* * * * *